United States Patent [19]

Hutson, Jr. et al.

[11] Patent Number: 4,581,474

[45] Date of Patent: Apr. 8, 1986

[54] HYDROCARBON CONVERSION PROCESS

[75] Inventors: Thomas Hutson, Jr., Galveston, Tex.; Paul D. Hann, Bartlesville, Okla.

[73] Assignee: Phillips Petroleum Company, Bartlesville, Okla.

[21] Appl. No.: 710,831

[22] Filed: Mar. 11, 1985

[51] Int. Cl.$^4$ .............................................. C07C 41/05
[52] U.S. Cl. .................................. 568/697; 585/314; 585/332
[58] Field of Search ................. 568/697; 585/332, 314

[56] References Cited

U.S. PATENT DOCUMENTS

| | | | |
|---|---|---|---|
| 3,726,942 | 4/1973 | Louder | 260/683.61 |
| 3,763,261 | 10/1973 | Sobel | 260/683.49 |
| 3,846,088 | 11/1974 | Brown | 44/56 |
| 3,912,463 | 10/1975 | Kozlowski | 44/56 |
| 4,270,929 | 6/1981 | Vu et al. | 44/56 |

Primary Examiner—Howard T. Mars
Attorney, Agent, or Firm—Howard D. Doescher

[57] ABSTRACT

In a combination alkylation-methyltertiary butyl ether (MTBE) operation, the unreacted $C_4$ olefinic hydrocarbons produced by etherification are contacted with molecular sieves to absorb 2-butenes and the 1-butenes remaining in the stream are divided so that one portion is subjected to double bond isomerization to form 2-butenes for alkylation and another portion is subjected to skeletal isomerization to form isobutene for etherification.

6 Claims, 1 Drawing Figure

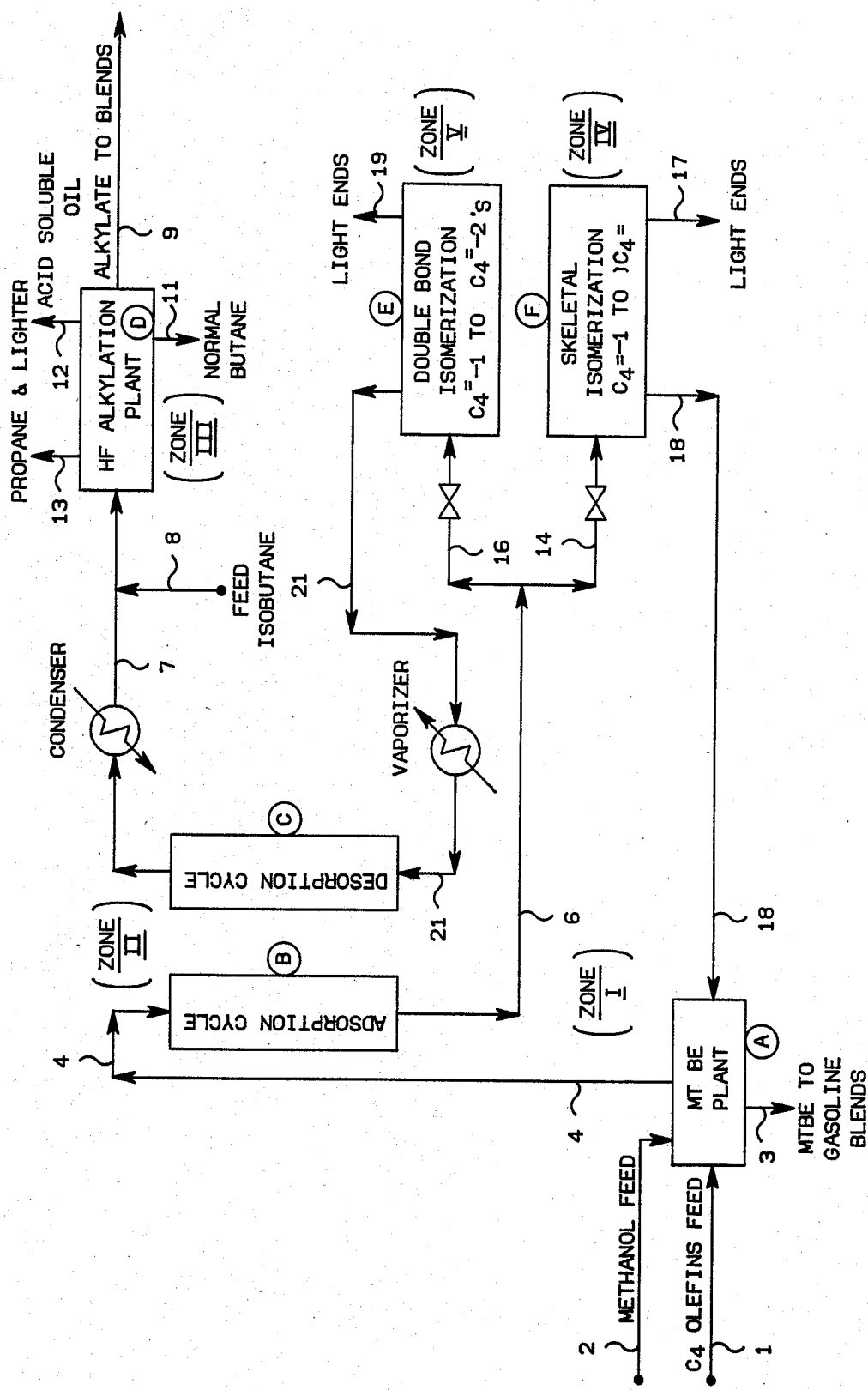

HYDROCARBON CONVERSION PROCESS

BACKGROUND OF THE INVENTION

This invention relates to the production of high octane blending components for gasolines. In another aspect, this invention relates to a combination process comprising etherification, isomerization, and alkylation together with appropriate fractionation and other separations for the production of tertiary alkyl ethers and alkylate gasoline which are high octane blending components for premium unleaded gasolines. In a further aspect, this invention relates to an etherification and alkylation process and the recovery of the produced hydrocarbon phase from etherification in a more efficient manner by treatment with a molecular sieve processing unit and parallel isomerization zones. In accordance with still another aspect, this invention relates to a combination type process including interrelationships of various streams from (a) methyl tertiary-alkyl ether manufacture, (b) molecular sieve processing, (c) parallel double bond and skeletal isomerizations, and (d) alkylation.

Accordingly, this invention is a combination process of known operations used herein in one specific embodiment in a novel manner so as to maximize the upgrading of the components of a butenes-containing stream to high octane tetraethyl lead (TEL)-free motor fuel in order to meet ultimate ecological requirements for high octane lead-free motor fuel.

Of the four butylene isomers, butene-1 produces the lowest octane value gasoline in HF catalytic aklylation with isobutane. Butenes-2 and isobutene make the highest octane value gasoline in HF catalytic alkylation. This system maximizes the use of isobutene for methyltertiarybutyl ether manufacture and maximizes the HF catalytic alkylation of butenes-2 with isobutane, with a minimizing of butene-1 in the alkylation.

Accordingly, an object of this invention is to produce high quality gasoline blending components from low boiling olefins.

Another object of this invention is to provide a combination process for the etherification and alkylation of low boiling olefins.

A further object of this invention is to maximize the production of isoolefins, such as isobutene, for ether manufacture as well as the production of olefins, such as 2-butenes, for alkylation.

Other objects, aspects, as well as the several advantages of the invention will be apparent to those skilled in the art upon consideration of the specification, the drawing, and the appended claims.

SUMMARY OF THE INVENTION

Thus, according to the invention, there is provided a combination etherification, isomerization, and alkylation process comprising subjecting olefins-containing hydrocarbon feedstocks to etherification, recovering a mixture of 1-olefin and 2-olefins from etherification, treating the mixture to molecular sieve processing to separate the 1-olefin therefrom, skeletal isomerizing at least a portion of the recovered 1-olefin to produce isoolefin for recycle to etherification, isomerizing the remaining portion of separated 1-olefin to 2-olefins, and passing the thus-produced 2-olefins to alkylation to form a high octane component for gasolines.

In accordance with one specific embodiment of the invention, in a process to produce MTBE (methyltertiarybutyl ether) and HF alkylate high octane blending stock from a C$_4$ olefin feed containing isobutylene, butene-1, butenes-2, isobutane and n-butane, the improvement comprises charging the overhead streams from the MTBE plant to a molecular sieve processing unit to separate butene-1 from butenes-2. A portion of butene-1 is skeletally isomerized to isobutene for recycle to MTBE plant. The remaining portion of butene-1 is double bond isomerized to butenes-2 which are combined with butenes-2 from mol sieve and sent to HF aklylation to produce alkylate with a feed containing isobutane. Alkylate is blended with MTBE to form high octane gasoline.

DETAILED DESCRIPTION OF THE INVENTION

The instant invention is primarily directed to an improved recovery and selective conversion system following a methyltert-alkyl ether process in which the production of 2-olefins, e.g., 2-butenes, is maximized for alkylation of an isoparaffin, e.g., isobutane, and at the same time supplies sufficient isoolefin, e.g., isobutene, for methyltertiarybutyl ether production, by eliminating low octane producing 1-olefin hydrocarbons in the etherification effluent, e.g., 1-butene, by isomerization in part to 2-butenes and in part to isobutene for use in alkylation and ether manufacture, respectively.

A better understanding of the invention will be obtained by reference to the accompanying drawing which shows an arrangement of an apparatus combination representing a preferred embodiment of the invention.

Various stream flow arrangements are illustrated on the drawing to show the flexibility of the operation for producing gasoline and gasoline blending components in an efficient manner.

DESCRIPTION OF THE INVENTION

Referring now to the drawing, a butenes-containing stream (comprising butene-1, butenes-2, and isobutene) from a catalytic cracking plant or other source, is charged via conduit (1) to a conventional methyltertiarybutyl ether (MTBE) plant A (Zone I) along with methanol via conduit (2) and along with an isobutene stream (18) from a skeletal isomerization (Zone IV) discussed hereinbelow. From the MTBE plant A (Zone I) MTBE is recovered via conduit (3) for use in gasoline blends as an octane enhancer. The MTBE reaction combines methanol with isobutene to make MTBE. The now linear butenes enriched stream from the MTBE plant A is passed via conduit (4) to butenes-2 adsorption B (Zone II).

The reaction between the C$_4$ cut and methanol is generally performed in the presence of an acid catalyst. The usual operating conditions are a temperature from about 0° to about 65° C. more often from about 10° to about 38° C. The etherification reaction is well-known.

In adsorption Zone B, a molecular sieve, as fully disclosed in U.S. Pat. No. 3,763,261, is utilized to adsorb butenes-2 from butene-1. Normally, at least two sieve units are used, one on adsorption of butenes-2 (adsorption unit B) and another on the desorption cycle to recover butenes-2 therefrom (desorption unit C). Details of flow pipes for alternating units B and C on the adsorption-desorption cycles are not shown in order to simplify this disclosure. Those versed in the adsorption-desorption art can very easily supply such piping and valves.

From adsorption unit B, on the adsorption cycle, the butene-1 stream (not adsorbed) is recovered via conduit (6).

From adsorption unit C, on the desorption cycle, the butenes-2 adsorbed during the use of unit C on its adsorption cycle, are desorbed using hot vaporized butenes-2 stream (21), from a source described hereinbelow, as the desorbing medium. The butenes-2 from unit C (including the desorbed butenes-2 and the butenes-2 utilized as the desorbing medium) are removed via (7), and after cooling and condensing to liquid, are passed as the butenes-2-rich olefin feed for conventional HF catalytic alkylation of isobutane in the alkylation plant D (Zone III). In addition, isobutane is charged via conduit (8) to the alkylation plant D. Herein, as is known by those skilled in the alkylation art, butenes-2 and isobutane react to produce extremely high octane alkylate when HF is used as the catalyst.

Details of the HF alkylation plant are not illustrated since such are well known to those skilled in this art. See, e.g., U.S. Pat. No. 4,059,649; U.S. Pat. No. 4,144,281; U.S. Pat. No. 4,105,707; among a plethora of patents in the HF alkylation field.

The alkylation reaction is conducted under conventional conditions for aliphatic alkylation. The alkylation is suitably carried out by the reaction of the mixture of hydrocarbons comprising isoparaffins containing from 4 to 8 carbon atoms and olefins containing 3 to 8 carbon atoms. The isoparaffins most commonly used as feedstock for motor gasoline alkylate are isobutane and isopentane. The olefins most commonly used are propylene and butenes. Preferred feedstocks currently are isobutane and a butylenes mixture. In this specific example, isobutane is reacted with the mainly straight chain butenes-2 remaining from the MTBE plant.

Referring again to the HF alkylation, wherein fractionation details are not shown, there are recovered acid soluble oils (12), normal butane (11) [which can be conventionally isomerized to isobutane and used as a part of the isobutane stream (8)], propane and lighter (13) and high octane alkylate product (9). This "butenes-2 alkylate", as is known in HF alkylation, is an extremely high octane blending component for gasolines and is especially valuable in producing tetraethyl lead (TEL)-free gasolines which will be required as the use of TEL is phased out due to ecological requirements.

Returning now to stream (6), which is the butene-1 rich steam: stream (6) is proportioned into stream (14) and stream (16) to produce therefrom isobutene and butenes-2, respectively. This proportioning relationship depends upon the demand for MTBE for gasoline blending. The example uses a 50—50 split for illustrative purposes. This split can vary, of course, depending on MTBE requirements.

That portion of butene-1 passed to isobutene production (skeletal isomerization) is charged to Zone IV, Unit F, via conduit (14). Light ends are recovered from Zone IV via conduit 17. Product isobutene is recovered from Zone IV via conduit (18) and is charged to MTBE production as previously described.

Another portion of stream (6) is passed via conduit (16) to double bond isomerization Zone V, Unit E, to convert butene-1 into butenes-2. From Zone V the light ends are removed via conduit (19), and butenes-2 product is removed via conduit (21) and used, at least in part, as desorption medium in unit C of Zone II. The desorbed butenes-2 and the butenes-2 removed from the sieve are charged to the HF alkylation Zone III as the olefin feed therefor.

The skeletal isomerization Zone IV is a conventional catalytic system for conversion of linear butenes, e.g., butene-1, into isobutene. The disclosure in U.S. Pat. No. 4,085,158 Column 9, lines 62 through line 29 of column 10, is sufficient to disclose the system of conversion of butene-1 to isobutene which is used in the process of our invention.

The double bond isomerization Zone V is also a conventional catalytic system to convert butene-1 to butenes-2. The disclosure in U.S. Pat. No. 4,085,158, column 9, line 11 through 59, is sufficient to disclose the system of conversion of butene-1 to butenes-2 which is used in the process of our invention.

EXAMPLE

In this example typical operations and units as illustrated in the drawing are set forth. The stream unit numbers in the example correspond to identical unit numbers in the drawing.

TABLE I

| | Units MLB/Day (Thousand Pounds/Day) | | | | | | | | |
|---|---|---|---|---|---|---|---|---|---|
| | ZONE I | | | | | | ZONE II | | |
| Stream No. | 1 | 2 | 18 | 4 | 3 | 6 | 21 | 7 | |
| | Olefin Feed | Methanol | Produced Isobutene | Unreacted Butenes | MTBE Product | Butene-1 Product | Butenes-2 (wo/desorbent) | Desor-Desorbent | Recovered $C_4=$ −2's & bent |
| Propane & Lighter | 4.61 | — | Trace | 4.61 | — | 4.61 | — | Trace | Trace |
| Isobutane | 63.88 | — | 68.60 | 132.68 | — | 130.65 | 1.83 | 64.47 | 66.30 |
| Normal Butane | 96.86 | — | 90.07 | 186.93 | — | 186.74 | 0.19 | 95.47 | 95.66 |
| Isobutene | 331.66 | — | 80.81 | 16.50 | — | 16.09 | 0.41 | 8.00 | 8.41 |
| Butene-1 | 244.26 | — | 80.82 | 325.08 | — | 316.95 | 8.13 | 47.78 | 55.91 |
| c,t.-butenes-2 | 275.05 | — | 1.75 | 276.80 | — | 5.54 | 271.26 | 111.37 | 382.63 |
| Butadiene | 9.60 | — | — | 8.01 | 1.59 | 0.16 | 7.85 | — | 7.85 |
| Water | 1.02 | 0.22 | — | 0.82 | — | 0.01 | 0.81 | — | 0.81 |
| Methanol | — | 222.70 | — | — | — | — | — | — | — |
| MTBE | — | — | — | — | 612.71 | — | — | — | — |
| Misc. | — | — | — | — | 6.38 | — | — | — | — |
| Alkylate | — | — | — | — | — | — | — | — | — |
| A.S.O. | — | — | — | — | — | — | — | — | — |
| TOTAL | 1,026.94 | 222.92 | 322.05 (c) | 951.23 | 620.68 | 660.75 (b) | 290.48 | 327.09 (d) | 617.57 (a) |
| | ZONE III | | | | ZONE IV | | ZONE V | | |

TABLE I-continued

| Stream No. | 8 | 11 | 9 | 12 | 13 | 14 | 17 | 18 | 16 | 19 | 21 |
|---|---|---|---|---|---|---|---|---|---|---|---|
| | Feed Isobutene | Normal Butane | HF Alkylate | ASO | Propane and Lighter | Feed | Light Ends | Isom. Product | Feed | Light Ends | Butenes-2 Product |
| Propane & Lighter | 6.01 | — | — | — | 6.01 | 2.30 | 5.70 | Trace | 2.31 | 2.43 | Trace |
| Isobutane | 412.52 | 2.50 | 1.50 | — | — | 65.33 | 1.60 | 68.60 | 65.32 | 0.86 | 64.47 |
| Normal Butane | 14.17 | 69.83 | 40.00 | — | — | 93.37 | 0.35 | 90.07 | 93.37 | — | 95.47 |
| Isobutene | — | — | — | — | — | 8.04 | Trace | 80.81 | 8.05 | — | 8.00 |
| Butene-1 | — | — | — | — | — | 158.47 | 0.66 | 80.82 | 158.48 | — | 47.78 |
| c,t.-butenes-2 | — | — | — | — | — | 2.77 | — | 1.75 | 2.77 | — | 111.37 |
| Butadiene | — | — | — | — | — | 0.08 | — | — | — | — | — |
| Water | — | — | — | 0.81 | — | — | — | — | — | — | — |
| Methanol | — | — | — | — | — | — | — | — | — | — | — |
| MTBE | — | — | — | — | — | — | — | — | — | — | — |
| Misc. | — | — | — | — | — | — | — | — | — | — | — |
| Alkylate | — | 2.50 | 923.91 | — | — | — | — | — | — | — | — |
| A.S.O. | — | — | — | 3.21 | — | — | — | — | — | — | — |
| TOTAL | 432.70 | 74.83 | 965.41 | 4.02 | 6.01 | 330.36 (b) | 8.31 | 322.05 (c) | 330.38 (b) | 3.29 | 327.09 (d) |

(a) Butenes-2 products from Zone II and Zone V (Conduit 7 is total) comprise HF alkylation olefin (rich in butenes-2) feed.
(b) The split of stream 6 is 50/50 in this illustration. Split is made so as to make desired amount of MTBE for plant gasoline blends.
(c) Butene-1 isomerization product (stream 18) is charged to MTBE plant of Zone I.
(d) Butenes-2 product (stream 21) is used to desorb sieve in Zone II.

After studying the above description, drawing, and typical operation of our invention, an engineer can readily see that there is herein presented a novel intercooperation of plant operations which optimizes the production of MTBE octane enhancer from isobutene, and which also maximizes the production of the high octane butenes-2 HF alkylate, thereby allowing a refiner to maximize the production of high octane gasoline blends which can be used TEL-free, to meet proposed ecological TEL-free requirements, as well as to meet high octane TEL-free automotive requirements.

That which is claimed is:

1. A combination process for producing high octane blending components for gasolines which comprises
   (a) contacting a mixture of methanol and an olefinic C$_4$ cut comprising isobutene, 1-butene, and 2-butenes under etherification conditions to produce methyltertiarybutyl ether and unreacted C$_4$ olefinic hydrocarbons,
   (b) contacting the unreacted C$_4$ olefinic hydrocarbons with a molecular sieve to selectively adsorb 2-butenes leaving a stream comprising 1-butene,
   (c) subjecting at least a portion of said 1-butene stream to skeletal isomerization to form isobutene,
   (d) subjecting the remainder of the 1-butene stream to double bond isomerization to form 2-butenes, and
   (e) passing the 2-butenes formed by isomerization and an isoparaffin to alkylation to form alkylate.

2. A process according to claim 1 wherein the 2-butenes formed in (d) are passed through a molecular sieve bed on desorption cycle to remove adsorbed 2-butenes for passing to alkylation in (e).

3. A process according to claim 1 wherein said alkylation is HF acid catalyzed and the isoparaffin is isobutane.

4. A process according to claim 1 wherein the isobutenes formed in (c) are passed to (a) as part of the feed.

5. A process according to claim 1 wherein the 2-butenes effluent from double bond isomerization is heated and then passed through a molecular sieve bed containing adsorbed 2-butenes under conditions to desorb 2-butenes therefrom, and passing double bond isomerization produced 2-butenes and desorbed 2-butenes and isobutane to an HF acid catalyzed alkylation.

6. A process according to claim 5 wherein isobutene produced by skeletal isomerization in (c) is recycled as part of the feed for etherification in (a).

* * * * *